(12) United States Patent
Hamburger et al.

(10) Patent No.: US 7,053,783 B2
(45) Date of Patent: May 30, 2006

(54) PATHOGEN DETECTOR SYSTEM AND METHOD

(75) Inventors: Robert N. Hamburger, San Diego, CA (US); Jian-Ping Jiang, Tucson, AZ (US); Richard D. O'Connor, San Diego, CA (US)

(73) Assignee: Biovigilant Systems, Inc., Tucson, AZ (US)

( * ) Notice: Subject to any disclaimer, the term of this patent is extended or adjusted under 35 U.S.C. 154(b) by 140 days.

(21) Appl. No.: 10/325,528

(22) Filed: Dec. 18, 2002

(65) Prior Publication Data
US 2006/0071803 A1    Apr. 6, 2006

(51) Int. Cl.
G08B 17/10    (2006.01)

(52) U.S. Cl. ............... 340/630; 340/507; 250/564; 250/574; 250/205; 250/222.2; 250/227.28; 356/438

(58) Field of Classification Search ........... 340/627, 340/630, 628; 250/564, 565, 573, 574; 356/337, 356/33 P, 439, 438; 73/28.01, 28.04, 863.21–863.24; 116/214
See application file for complete search history.

(56) References Cited

U.S. PATENT DOCUMENTS

| | | |
|---|---|---|
| 3,845,480 A | 10/1974 | Steinberg |
| 3,867,640 A | 2/1975 | Paulson |
| 4,175,865 A | 11/1979 | Horvath et al. |
| 4,177,482 A * | 12/1979 | Henry .................. 348/131 |
| 4,226,533 A | 10/1980 | Snowman |
| 4,286,876 A | 9/1981 | Hogg et al. |
| 4,583,859 A | 4/1986 | Hall, II |
| 4,728,190 A | 3/1988 | Knollenberg |
| 4,737,648 A | 4/1988 | Smith et al. |
| 4,830,494 A | 5/1989 | Ishikawa et al. |
| 4,839,529 A | 6/1989 | Fruengel |
| 4,940,326 A * | 7/1990 | Tatsuno .................. 356/336 |
| 5,006,986 A | 4/1991 | Inoue |
| 5,083,865 A | 1/1992 | Kinney et al. |
| 5,085,500 A | 2/1992 | Blesener |

(Continued)

FOREIGN PATENT DOCUMENTS

EP          435166          7/1991

(Continued)

OTHER PUBLICATIONS

"Continuous, Rapid Biological Aerosol Detection with the Use of Fluorescence: Outdoor Test Results" Eversole et al., Field Analytical Chemistry and Technology 3(4-5):249-259, 1999.

(Continued)

Primary Examiner—Benjamin C. Lee
(74) Attorney, Agent, or Firm—Hayes Soloway P.C.

(57) ABSTRACT

A pathogen detector has a sample area for containing environmental air, a light source on one side of the sample area for directing a collimated beam of light through the sample air so that part of the light beam will be scattered by any particles present in the air while the remainder remains unscattered, and a beam blocking device on the opposite side of the sample area for blocking at least the unscattered portion of the beam of light and directing at least part of the scattered light onto a detector. The detector produces output pulses in which each pulse has a height proportional to particle size and a pulse height discriminator obtains the size distribution of airborne particles detected in the air sample at a given time from the detector output. An alarm signal is activated if the number of particles within a predetermined pathogen size range of around 1 to 7 μm exceeds a predetermined normal level.

18 Claims, 4 Drawing Sheets

U.S. PATENT DOCUMENTS

| | | | |
|---|---|---|---|
| 5,101,113 A | 3/1992 | Hirleman, Jr. et al. | |
| 5,117,357 A | 5/1992 | Inoue | |
| 5,121,988 A | 6/1992 | Blesener et al. | |
| 5,123,731 A | 6/1992 | Yoshinaga et al. | |
| 5,125,737 A | 6/1992 | Rodriguez et al. | |
| 5,132,548 A | 7/1992 | Borden et al. | |
| 5,166,537 A | 11/1992 | Horiuchi et al. | |
| 5,180,065 A | 1/1993 | Touge et al. | |
| 5,231,378 A | 7/1993 | Dennis et al. | |
| 5,257,087 A * | 10/1993 | Furuya | 356/336 |
| 5,266,798 A | 11/1993 | Borden et al. | |
| 5,286,452 A | 2/1994 | Hansen | |
| 5,305,072 A | 4/1994 | Sawada et al. | |
| 5,315,115 A | 5/1994 | Gerber | |
| 5,366,858 A | 11/1994 | Koizumi et al. | |
| 5,383,024 A | 1/1995 | Maxey et al. | |
| 5,416,580 A | 5/1995 | Trainer | |
| 5,426,501 A | 6/1995 | Hokanson et al. | |
| 5,428,964 A | 7/1995 | Lobdell | |
| 5,448,364 A | 9/1995 | Moran | |
| 5,456,102 A | 10/1995 | Moorehead | |
| 5,457,526 A | 10/1995 | Kosaka | |
| 5,481,357 A | 1/1996 | Ahsan et al. | |
| 5,506,673 A | 4/1996 | Kosaka et al. | |
| 5,561,515 A | 10/1996 | Hairston et al. | |
| 5,600,438 A | 2/1997 | Kreikebaum et al. | |
| 5,646,597 A | 7/1997 | Hamburger et al. | 340/627 |
| 5,684,585 A | 11/1997 | Girvin | |
| 5,864,399 A | 1/1999 | Girvin et al. | |
| 5,943,130 A * | 8/1999 | Bonin et al. | 356/336 |
| 5,946,093 A | 8/1999 | DeFreez et al. | |
| 5,969,622 A | 10/1999 | Hamburger et al. | |
| 5,986,555 A | 11/1999 | Hamburger et al. | |
| 5,995,686 A | 11/1999 | Hamburger et al. | 385/12 |
| 6,008,729 A | 12/1999 | Hamburger et al. | |
| 6,087,947 A | 7/2000 | Hamburger et al. | 340/627 |
| 6,386,015 B1 | 5/2002 | Rader et al. | |
| 2001/0012429 A1 | 8/2001 | Wach et al. | 385/115 |
| 2001/0024800 A1 | 9/2001 | Garcia-Rubio et al. | 435/7.21 |
| 2002/0028519 A1 | 3/2002 | Yguerabide et al. | 436/518 |
| 2002/0032165 A1 | 3/2002 | Johnson et al. | 514/44 |
| 2002/0045276 A1 | 4/2002 | Yguerabide et al. | 436/518 |
| 2002/0046966 A1 | 4/2002 | Muscate-Magnussen | 210/198.2 |
| 2002/0065468 A1 | 5/2002 | Utzinger et al. | 600/476 |
| 2002/0103517 A1 | 8/2002 | West et al. | 607/88 |
| 2002/0119486 A1 | 8/2002 | Oberhardt | 435/6 |
| 2002/0132766 A1 | 9/2002 | DeGrado et al. | 514/12 |
| 2002/0135752 A1 | 9/2002 | Sokolov et al. | 356/39 |
| 2002/0143243 A1 | 10/2002 | Georgakoudi et al. | 600/310 |
| 2002/0165456 A1 | 11/2002 | Canpolat et al. | 600/473 |
| 2002/0171831 A1 | 11/2002 | Backman et al. | 356/369 |
| 2003/0013973 A1 | 1/2003 | Georgakoudi et al. | 600/473 |
| 2003/0022249 A1 | 1/2003 | Schmitz et al. | 435/7.21 |
| 2003/0030783 A1 | 2/2003 | Roche et al. | 356/39 |
| 2003/0052281 A1 | 3/2003 | Rader et al. | 250/461.1 |
| 2003/0077627 A1 | 4/2003 | Worthington et al. | 435/6 |
| 2003/0093092 A1 | 5/2003 | West et al. | 606/139 |
| 2003/0096302 A1 | 5/2003 | Yguerabide et al. | 435/7.1 |
| 2003/0098421 A1 | 5/2003 | Ho | 250/458.1 |
| 2003/0098422 A1* | 5/2003 | Silcott et al. | 250/458.1 |
| 2003/0124733 A1 | 7/2003 | Bushway et al. | 436/174 |
| 2003/0137669 A1 | 7/2003 | Rollins et al. | 356/479 |
| 2003/0139886 A1 | 7/2003 | Bodzin et al. | 702/28 |
| 2003/0157731 A1 | 8/2003 | Yaguerabide et al. | 436/523 |
| 2003/0157732 A1 | 8/2003 | Baker et al. | 436/531 |
| 2003/0159498 A1 | 8/2003 | Small | 73/24.02 |
| 2003/0207328 A1 | 11/2003 | Yguerabide et al. | 435/7.1 |
| 2003/0223063 A1 | 12/2003 | Hill et al. | 356/340 |
| 2003/0228682 A1 | 12/2003 | Lakowicz et al. | 435/287.2 |
| 2003/0231309 A1 | 12/2003 | Fulghum, Jr. et al. | 356/338 |
| 2003/0232445 A1 | 12/2003 | Fulghum, Jr. | 436/63 |
| 2004/0009941 A1 | 1/2004 | Johnson et al. | 514/44 |
| 2004/0011975 A1* | 1/2004 | Nicoli et al. | 250/574 |
| 2004/0021861 A1 | 2/2004 | Lewis et al. | 356/326 |
| 2004/0023317 A1 | 2/2004 | Motamedi et al. | 435/14 |
| 2004/0038413 A1 | 2/2004 | Kramer | 436/63 |
| 2004/0057050 A1 | 3/2004 | Beck et al. | 356/336 |
| 2004/0072356 A1 | 4/2004 | Senisterra et al. | 436/63 |
| 2004/0073120 A1 | 4/2004 | Motz et al. | 600/478 |
| 2004/0079893 A1 | 4/2004 | Dietz et al. | 250/458.1 |
| 2004/0161143 A1 | 8/2004 | Dietz et al. | 382/133 |
| 2004/0197232 A1 | 10/2004 | Kramer | 422/73 |
| 2004/0218184 A1 | 11/2004 | Jorgenson et al. | 356/419 |
| 2005/0019842 A1 | 1/2005 | Prober et al. | 435/7.9 |
| 2005/0057749 A1 | 3/2005 | Dietz et al. | 356/318 |
| 2005/0073683 A1 | 4/2005 | Gard et al. | 356/337 |
| 2005/0112784 A1 | 5/2005 | Yguerabide et al. | 436/518 |
| 2005/0130324 A1 | 6/2005 | West et al. | 436/523 |

FOREIGN PATENT DOCUMENTS

| | | |
|---|---|---|
| EP | 595290 | 10/1993 |
| EP | 618440 | 10/1994 |
| EP | 711991 | 5/1996 |
| EP | 463795 | 11/1996 |
| EP | 214769 | 3/1997 |
| EP | 475748 | 11/1997 |
| EP | 737307 | 8/1998 |
| EP | 1158292 A2 | 11/2001 |
| GB | 1296658 | 12/1972 |
| GB | 1298658 | 12/1972 |
| JP | 63-321108 | 6/1990 |
| JP | 04-185654 | 1/1994 |
| WO | 91/10123 | 7/1991 |
| WO | 93/16368 | 8/1993 |
| WO | 95/09354 | 4/1995 |

OTHER PUBLICATIONS

"Bio-Aerosol Fluorescence Sensor" Jeys et al., Proc. IRIS Active Systems, 1998, vol. 1, p. 235-249.

* cited by examiner

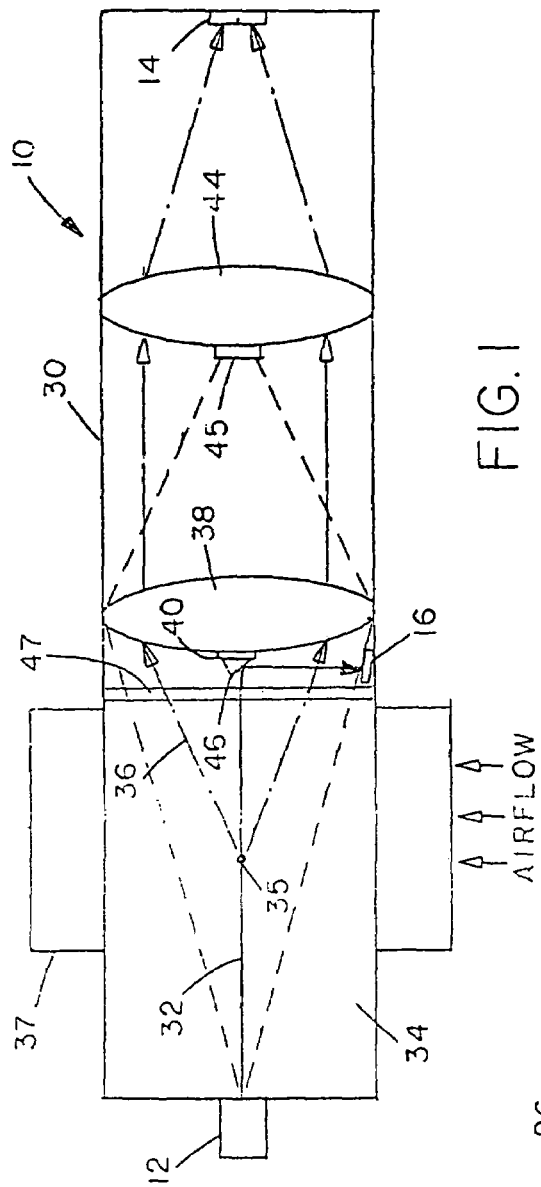
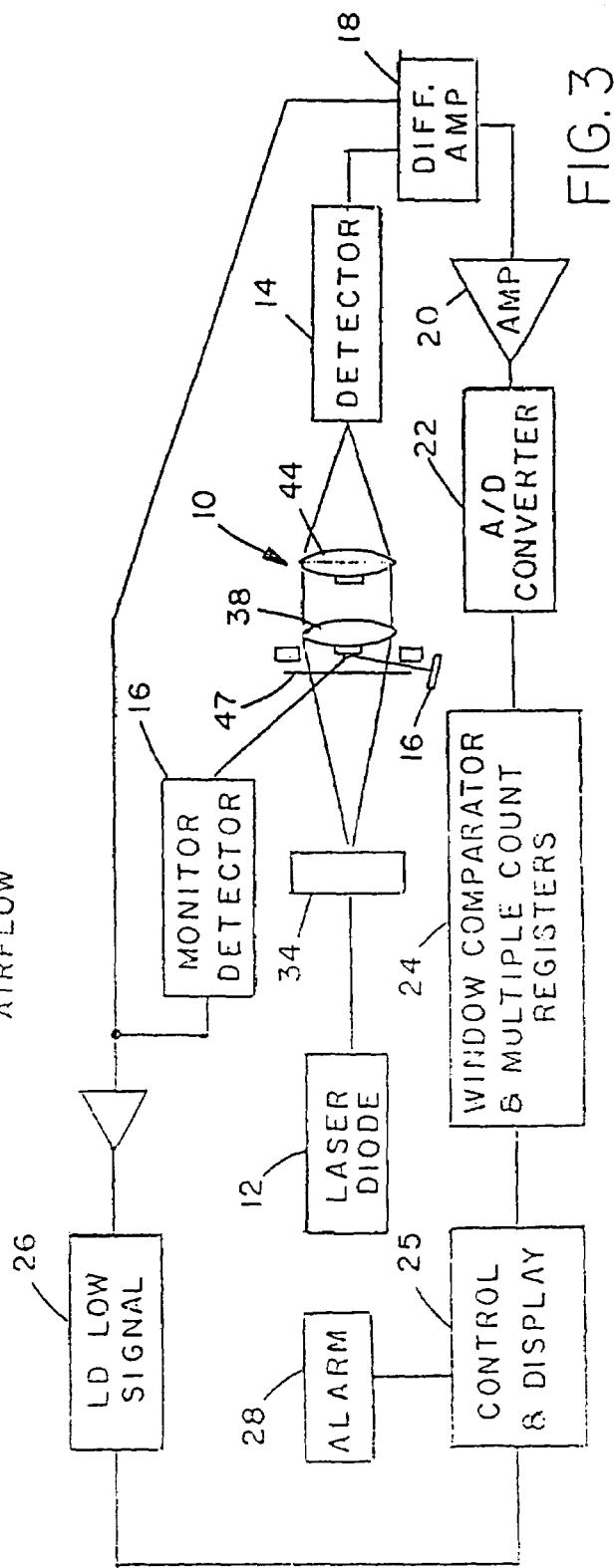
FIG. 1
FIG. 3

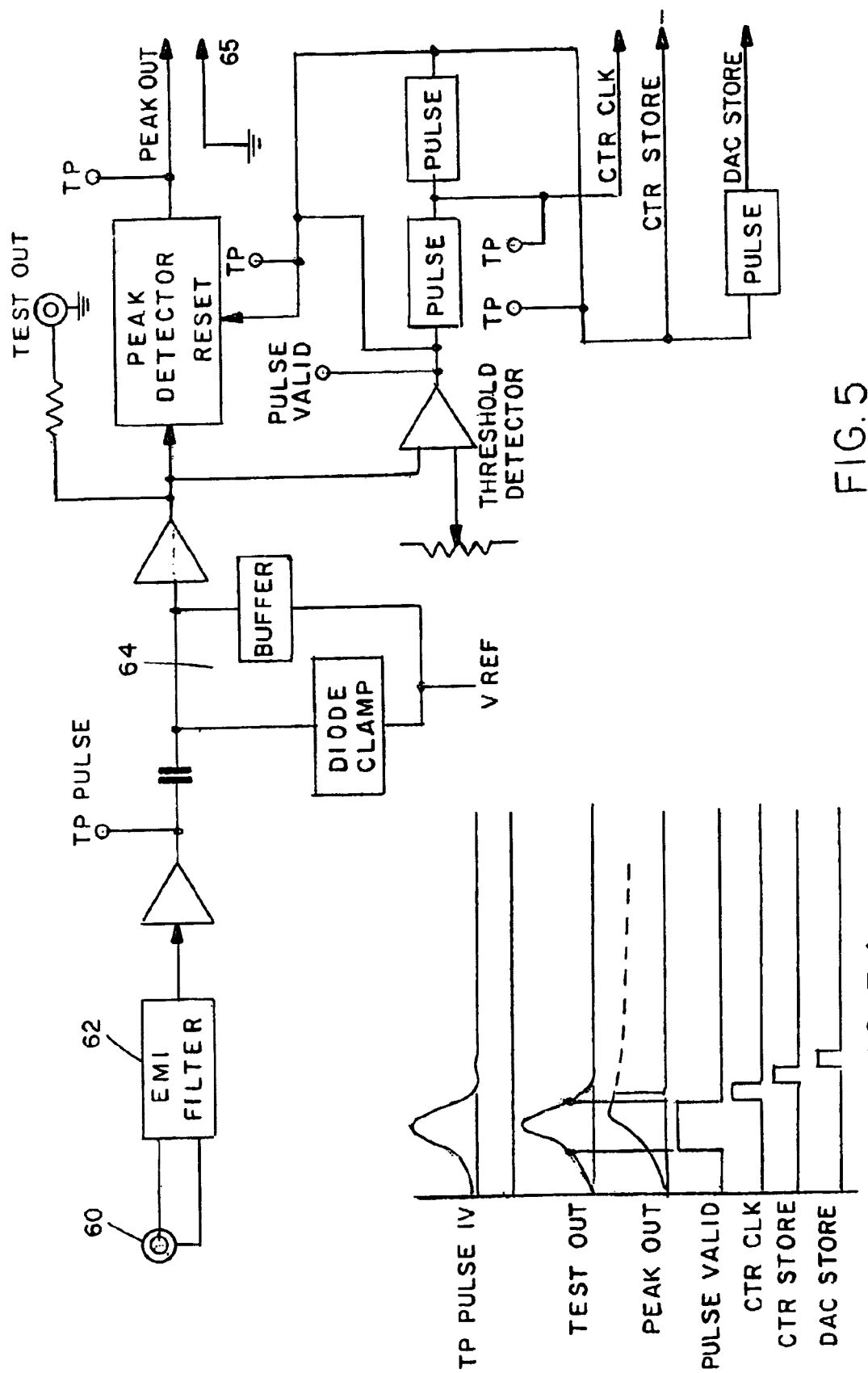

PATHOGEN DETECTOR SYSTEM AND METHOD

BACKGROUND OF THE INVENTION

The present invention relates to a pathogen detector system and method.

An urban terrorist attack involving release of biological warfare agents such as *bacillus anthracis* (anthrax) is presently a realistic concern. Weaponized anthrax spores are extremely dangerous because they can gain passage into the human lungs. A lethal inhalation dose of anthrax spores for humans, $LD_{50}$ (lethal dose sufficient to kill 50% of the persons exposed) is estimated to be 2,500 to 50,000 spores (see T. V. Inglesby, et al., "Anthrax as a Biological Weapon", JAMA, vol. 281, page 1735, 1999). Some other potential weaponized bio-agents are *yersinia pestis* (plague), *clostidium botulinum* (botulism), and *francisella tularensis*. In view of this potential threat, there is currently a need for an early warning system to detect such an attack. At this point, there is no detection device or system for detecting airborne pathogens which is sufficiently sensitive, inexpensive, and rugged enough for field deployment.

Laser particle counters are known in which a laser beam is directed through a sample and the light which travels through the sample is detected and analyzed to detect scattered light from particles in the sample. One problem with existing detectors or particle counters which are designed for detection of scattered light is that the scattering signal must be extracted from the incident illumination light source signal. This involves detecting a weak signal (scattering from small particles) from a very noisy background (glare from the laser source). This feature has long caused major difficulty in the instrumentation of laser particle counters. Conventionally designed laser particle counters employ costly and elaborate means to reduce the glare from the laser illumination source and to measure particle scattering against a large background noise, rendering the counters fragile and expensive. Currently, conventionally designed laser particle counters are fragile and expensive, and unsuited to this application. The conventional techniques used for laser particle counting include the laser Doppler method, which measures the speed of the particle and deduces size information, the transient time method which measures the time needed for particles to traverse a sensing region, and large angle multi-sensor design, which is capable of measuring only small particles. A proposed bio-sensor based on laser-induced fluorescence using a pulsed UV laser is described by T. H. Jeys, et al., Proc. IRIS Active Systems, vol. 1, p. 235, 1998. This is capable of detecting an aerosol concentration of five particles per liter of air, but involves expensive and delicate instruments. Other particle counters are manufactured by Met One Instrument, Inc, of Grants Pass, Oreg., Particle Measurement Systems, Inc., of Boulder, Colo., and Terra Universal Corp., of Anaheim, Calif. By virtue of their design, these particle counter configurations require precision optical alignment, as well as sophisticated sensors and electronics. These products are geared towards laboratory use and cost thousands of dollars for a single unit. Thus, they are not suitable for a field deployed detector, nor are they designed specifically for detection of biological warfare agents.

Various detectors have been designed to detect airborne allergen particles and provide warning to sensitive individuals when the number of particles within an air sample exceeds a predetermined minimum value. These are described in U.S. Pat. Nos. 5,646,597, 5,969,622, 5,986,555, 6,008,729, and 6,087,947, all of Hamburger et al. These detectors all involve direction of a light beam through a sample of environmental air such that part of the beam will be scattered by any particles in the air, a beam blocking device for transmitting only light scattered in a predetermined angular range corresponding to the predetermined allergen size range, and a detector for detecting the transmitted light. An alarm is actuated if the light detected at the detector is above a predetermined level. Although these devices are sufficient for the purpose of providing an alarm indication based on the presence of allergen particles, they are not suitable for field deployment and do not meet the more stringent requirements for a pathogen detector for detecting biological warfare agents.

SUMMARY OF THE INVENTION

It is an object of the present invention to provide a new and improved pathogen detector system and method for detecting airborne pathogens or airborne bio-agents.

According to one aspect of the present invention, a pathogen detector system is provided, which comprises an outer housing having a sample area for containing environmental air, a light source for directing a focused beam of light through the sample air, whereby portions of the beam of light are scattered at various angles by particles of various sizes present in the sample area, and an unscattered portion of the beam of light remains unscattered, a beam blocking device for blocking at least the unscattered portion of the beam of light and directing at least part of the scattered light along a light path, a detector positioned in the light path after the beam blocking device for detecting light directed by the beam blocking device onto the detector, and producing output pulses in which each pulse has a height proportional to particle size, a pulse height discriminator for obtaining the size distribution of airborne particles in the air sample at a given time, and an alarm unit for providing a warning signal if the number of particles within a predetermined pathogen size range of approximately 1 to 7 microns is exceeded.

In an exemplary embodiment of the invention, the output of the pulse height discriminator is connected to a processing unit for processing the particle size distribution at a given time, based on the height of each pulse, producing a histogram of the airborne particle size distribution, and displaying the histogram on an output device. The discriminator may comprise a peak detector for measuring incoming pulse height, and a comparator and register for registering the number of pulses in each pulse height. The respective pulse heights are then converted into particle sizes, and a histogram of the particle size distribution is displayed on a suitable display unit, such as an LED or liquid crystal display, or a computer screen.

An alarm device may also be provided to produce an audible and/or visible alarm signal if the number of pulses in a certain particle size range exceeds a predetermined normal background value. Any sudden and localized increase in the number of airborne particle counts in the size range from 1 µm to 7 µm would normally signify an intentional release of hostile bio-agents.

In an exemplary embodiment of the invention, a reflector is placed on or in front of the beam blocker in order to reflect part of the unscattered portion of the incident light beam, and a second photodetector is positioned to detect light reflected from the reflector. The function of the photodetector is to monitor the output of the light source, which may be a laser diode. This allows for self-calibration of the apparatus. The particle size measurement relies on the electrical pulse height measurement, and it is therefore important to account for any fluctuations in the laser diode power output. The electrical pulse signal from the first detector may be divided by the monitoring signal from the second detector in order to ensure that the results are not affected by any laser power variations. The output of the second photodetector is also monitored to indicate the laser diode performance. When the signal from the second photodetector falls below a predetermined level, such as 50% of the starting power level, a "Laser Power Low" alarm will sound, in order to initiate a maintenance call.

A transparent partition slide may be provided between the sample area and the beam blocking device. The purpose of the slide is to prevent dust or other environmental pollutants from reaching the optical elements and photodetectors. This will be particularly beneficial when the system is used in harsh field deployment conditions. The slide is replaced when it becomes too dirty to allow sufficient light transmission, which will be determined by the second photodetector. Thus, the laser power alarm may indicate either that the laser diode has lost power, or that the slide has become too dirty. A moderately dirty partition slide will not affect the accuracy of particle detection, since it will reduce the light intensity of both the unscattered portion of the light beam and the scattered light beam, and the ratio of these two signals is recorded.

According to another aspect of the present invention, a method of detecting airborne pathogens is provided, which comprises the steps of:

directing a light beam through a sample of environmental air such that a first portion of the light beam is scattered by particles present in the sample and a second portion remains unscattered;

receiving both portions of the light beam which have passed through the air sample and directing the light beam portions onto a beam blocking device;

blocking at least the second portion of the light beam at the beam blocking device and directing at least part of the first portion of the light beam onto a first detector;

measuring the pulse height of electrical pulses output from the first detector;

counting the number of pulses of each pulse height in a predetermined time interval;

converting the pulse heights to particle sizes;

counting number of pulses corresponding to each particle size; and producing an alarm signal if the number of pulses detected within a predetermined size range corresponding to pathogen-size particles is exceeded.

As noted above, the size range for airborne, weaponized pathogens or bio-agents is from approximately 1 μm to 7 μm. The same method may alternatively be used to detect other harmful airborne substances, such as beryllium or asbestos dusts. Environmental air is continuously blown through the sample area so that the environmental air is constantly monitored for changes in the number of pathogen-size particles. Clearly, there may be the same low levels of harmless particles in the monitored size range, but any sudden increase in the numbers in this particular size range would indicate deliberate or accidental release of airborne pathogens.

In an exemplary embodiment of the invention, the data regarding number of pulses for each particle size is converted into a histogram of the detected particle size distribution. This may then be compared to known bio-agent particle size distributions, and an alarm may be activated if the detected distribution matches any known bio-agent particle size distribution. The size distribution may also be used to identify the particular bio-agent detected, and provides a forensic tool for identifying the manufacturing process by which the weaponized bio-agent was produced.

The pathogen detection system and method of this invention can be used to detect the presence of airborne biological warfare agents or other harmful substances. The beam blocking device will stop the unscattered incident laser beam, efficiently eliminating the background noise caused by the light source, and then detecting the angular distribution and intensity of light scattered by particles in an air sample, converting the output of the detector into a particle size distribution histogram, and producing an alarm signal if the histogram indicates unusually large numbers of particles within a predetermined airborne pathogen size range. The detector system is sensitive, inexpensive, and rugged enough for field deployment. Although the system does not necessarily detect the exact species of pathogen, it can provide a sensitive and cost effective early warning of a bio-agent attack. It can also be arranged to provide early warning of other harmful airborne particles which may case pulmonary distress, such as asbestos and beryllium dusts.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which:

FIG. 1 is a schematic block diagram of the optical portion of an airborne pathogen detector system according to an exemplary embodiment of the invention;

FIG. 3 is a block diagram of the pathogen detector system according to an exemplary embodiment of the invention, incorporating the optical system of FIG. 1;

FIG. 5 is a schematic diagram of the analog to digital converter portion of the circuit of FIG. 4;

FIG. 5A is a diagram illustrating pulse wave forms at various points in the circuit.

DETAILED DESCRIPTION OF THE DRAWINGS

Figure 6:
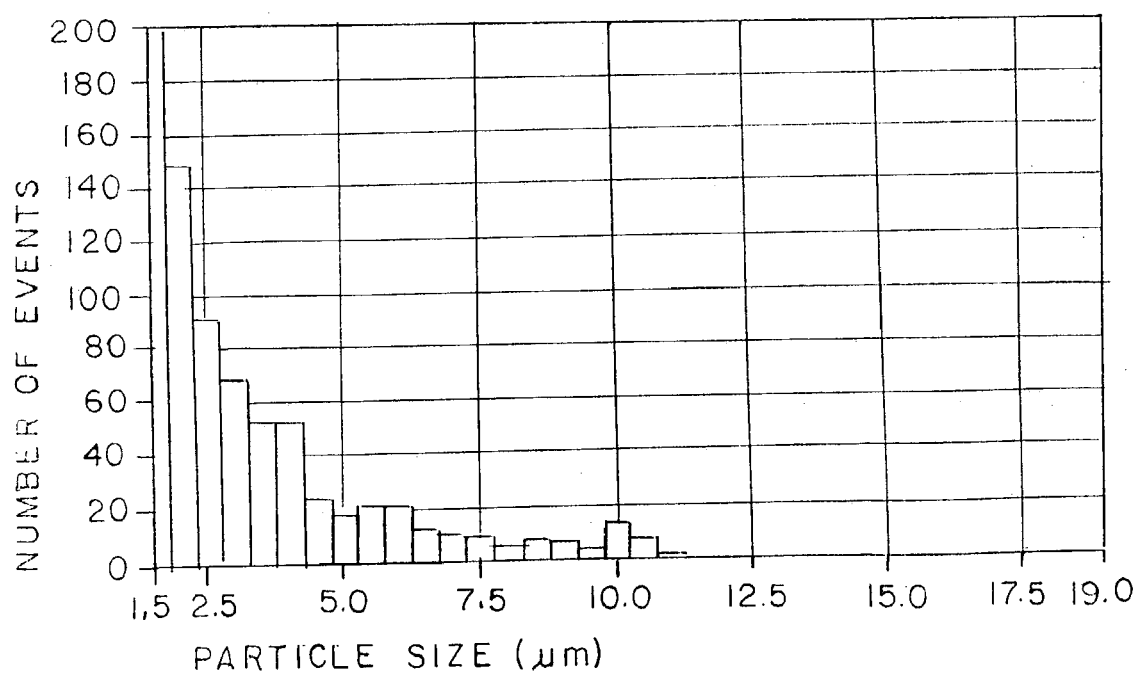
FIG. 6 illustrates an exemplary output histogram displayed by the system of FIGS. 3 and 4 in a situation where the pathogen-size particle counts exceed a predetermined amount, triggering an alarm condition.

FIGS. 1 and 3 to 5 illustrate an airborne pathogen detector system according to an exemplary embodiment of the invention, while FIG. 6 illustrates an exemplary output from the system. The term "pathogen" here refers to any airborne particles which could potentially harm or even kill humans exposed to such particles if present in the air in sufficient quantities. The system is particularly intended to detect airborne bio-terrorist agents deliberately released by terrorists or others, but may also be used in civilian applications to detect harmful levels of other airborne particles which may have been accidentally released, such as asbestos or beryllium dusts.

The detector system is designed to detect airborne particles within a specific size range, and to produce an output indicating the number of particles of each size within the range which is detected in a sample, and also to produce an alarm signal if the number of particles exceeds a predetermined value above a normal background level. As illustrated in FIGS. 1 and 3, the system basically comprises an optical unit 10, a laser diode or other light source 12 directing a light beam into the optical unit, a first photodetector 14 at the output of optical unit detecting light transmitted through the unit, a second photodetector 16 for detecting the light output of the laser diode, a differential amplifier 18 for dividing the output of photodetector 14 by the output of photodetector 16, an amplifier 20 connected to the output of differential amplifier 18, an analog to digital converter 22, a window comparator circuit 24, and a control and output display unit connected to the output of circuit 24. A low signal detection circuit 26 is connected to the output of photodetector 16 which detects the laser diode power, and the output of circuit 26 is also connected to control unit 25. An alarm device 28 is also connected to computer 25.

The optical portion 10 of the system will now be described in more detail with reference to FIG. 1. This portion is similar to the optical system described in U.S. Pat. Nos. 5,986,555 and 6,087,947 of Hamburger et al., the contents of which are incorporated herein by reference. The optical system will be contained in an outer housing 30 which may be of tubular or other shapes. The light source 12 directs a collimated laser light beam 32 through an air sample region 34 within the housing. When the collimated light beam strikes particles 35 within the air sample, a portion of the beam is deflected or scattered, with the angle of deflection being dependent on the size of the particle. Scattered portions 36 of the light beam therefore represent the presence of particles within the air sample. Environmental air is constantly drawn through the sample region 34 in the direction of the arrows in FIG. 1 by a fan unit 37, in the same way as described in the patents referenced above.

A lens 38 is located in the housing in the path of both the unscattered and scattered portions of the light beam exiting the sample area. The lens 38 has a central, blocking member 40 of predetermined diameter which is designed to absorb light. In an exemplary embodiment, blocking member 40 was a black piece of vinyl adhered to the front of lens 38, although other beam blocking devices may alternatively be used. The diameter of member 40 is such that at least the unscattered portion of the focused light beam is blocked and prevented from traveling any further through unit 10. The diameter of circular blocking member 40 may be about 2 mm. greater than the diameter of the unfocused light beam, and may be designed such that it blocks unscattered light and light scattered by particles larger than a predetermined size, such as 50 microns. An even larger blocking member may be used to further eliminate light scattered by particles smaller than 50 microns, if desired. The lens may also have an annular ring (not illustrated) of light blocking material surrounding the central blocking member 40 as described, for example, in U.S. Pat. No. 6,087,947 referred to above. This will act to block light scattered by particles smaller than a predetermined minimum value. However, the lens and housing diameter may alternatively be designed such that light scattered by such particles will not be transmitted.

Figure 2:
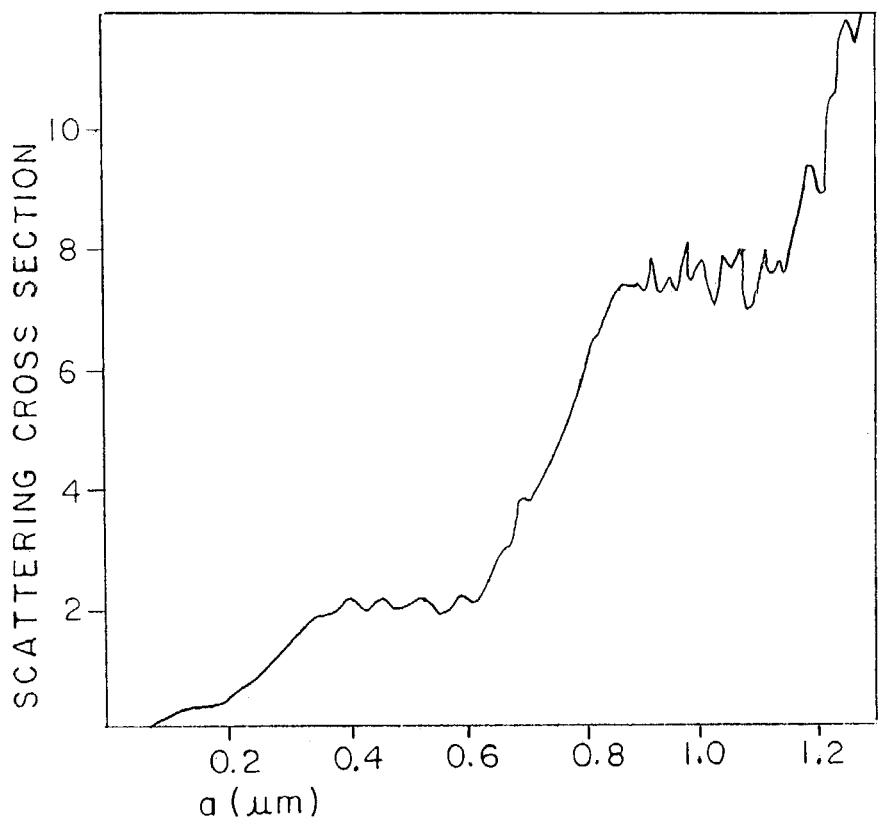
FIG. 2 is a graph illustrating the relationship of Mie scattering cross-section of incident light to the airborne particle size.

In the prior patents discussed above, the beam blocking device comprising the lens 38 and beam blocking member 40 (and annular beam blocking ring if present) was designed to block transmission of light scattered by particles outside a predetermined allergen particle size range of 5 to 50 microns. However, the present apparatus is intended to detect particles in a different size range, specifically airborne biological warfare agents or harmful dusts. Since the size of such particles may be as low as 0.5 μm, the lens 38, housing 30, and beam blocking member 40 are of predetermined dimensions such that light transmitted by particles outside a size range of 0.5 μm to 50 μm will be blocked, while portions 42 of the light beam scattered by particles within the size range of 0.5 μm to 50 μm are transmitted through the annular ring portion of the lens which surrounds blocking member 40. It will be understood that the dimensions of the blocking member may be varied if desired to further limit the portion of the light beam transmitted through lens 38.

Light source 12, in addition to the focused light beam 32, also generates a certain amount of noise from its surface. Such noise is focused by lens 38 onto a circular blocking member 45 at the center of the second lens 44, such that it is blocked from reaching the detector 14. However, the scattered portions of the light beam transmitted by lens 38 are focused by lens 44 onto detector 14 as indicated in FIG. 1. Circular blocking member 45 may be identical to blocking member 40.

Optical unit 10 differs from the optical units described in the aforementioned two patents in the following respects. First, a reflector 46 is placed on or in front of the beam blocking member 40. The reflector may be a tilted mirror or a coated prism set. This reflector is designed to reflect the unscattered, incident laser beam onto the second, or monitoring, photodetector 16. Secondly, a transparent partition slide 47 is placed between the sample area 34 and the beam blocking device 38,40. The purpose of the slide is to prevent dust or other environmental pollutants from reaching the optical elements and photodetectors. This will be particularly beneficial when the system is used in harsh field deployment conditions. The slide is removably mounted in the housing so that it can be replaced when it becomes too dirty to allow sufficient light transmission, which will be determined by the second photodetector. Thus, the laser power alarm may indicate either that the laser diode has lost power, or that the slide has become too dirty. A moderately dirty partition slide will not affect the accuracy of particle detection, since it will reduce the light intensity of both the unscattered portion of the light beam and the scattered light beam, and the ratio of these two signals is recorded.

Although the beam "blocking" device in the illustrated embodiment is a lens having a central blocking region and optionally also an outer blocking ring, such that only light scattered in a predetermined angular region is transmitted to the lens, the blocking device in alternative embodiments may be a concave mirror having a central light absorbing light blocker as above, or a central opening of predetermined diameter. The detector 14 in this case will be positioned to detect light reflected from the concave mirror, as described in U.S. Pat. No. 6,008,729 of Hamburger et al., the contents of which are also incorporated herein by reference. An angled mirror or prism may still be used in exactly the same way as illustrated in FIG. 1 in order to direct part of the unscattered portion of the beam onto the second detector.

The system design is based upon the principle of Mie scattering of light by particles with sizes comparable with the wavelength of light. In the Mie scattering regime, both the angular distribution and the intensity of the scattered light are strongly dependent on the particle size and shape. Mie scattering is characterized by the following properties: 1) The scattered light is concentrated in the forward direction; 2) the angular distribution of the scattered light intensity is highly sensitive to the scattering particle size; 3) the scattering cross-section of a particle is proportional to the particle size in a monotonic but complex manner. Using visible light, such as a visible laser diode light output beam of wavelength 0.67 µm, the Mie scattering method is ideally suited for detecting and characterizing airborne particles in the micron size range. The relationship of Mie scattering cross-section to particle radius is shown in FIG. 2.

The optical unit 10 of the system uses the principle that scattering angle is proportional to particle size in order to eliminate light scattered outside a predetermined range using a beam blocking device 36 positioned in the path of light which has traveled through the sample. The remainder of the system is designed to detect the particle size distribution in the sample by discriminating between pulses of different heights detected at detector 14, since the scattering cross section of a particle is proportional to the particle size in a monotonic but complex manner, as described above and illustrated in FIG. 2. Therefore, the heights of the electrical pulses output from detector 14 are dependent on particle size.

Figure 4:
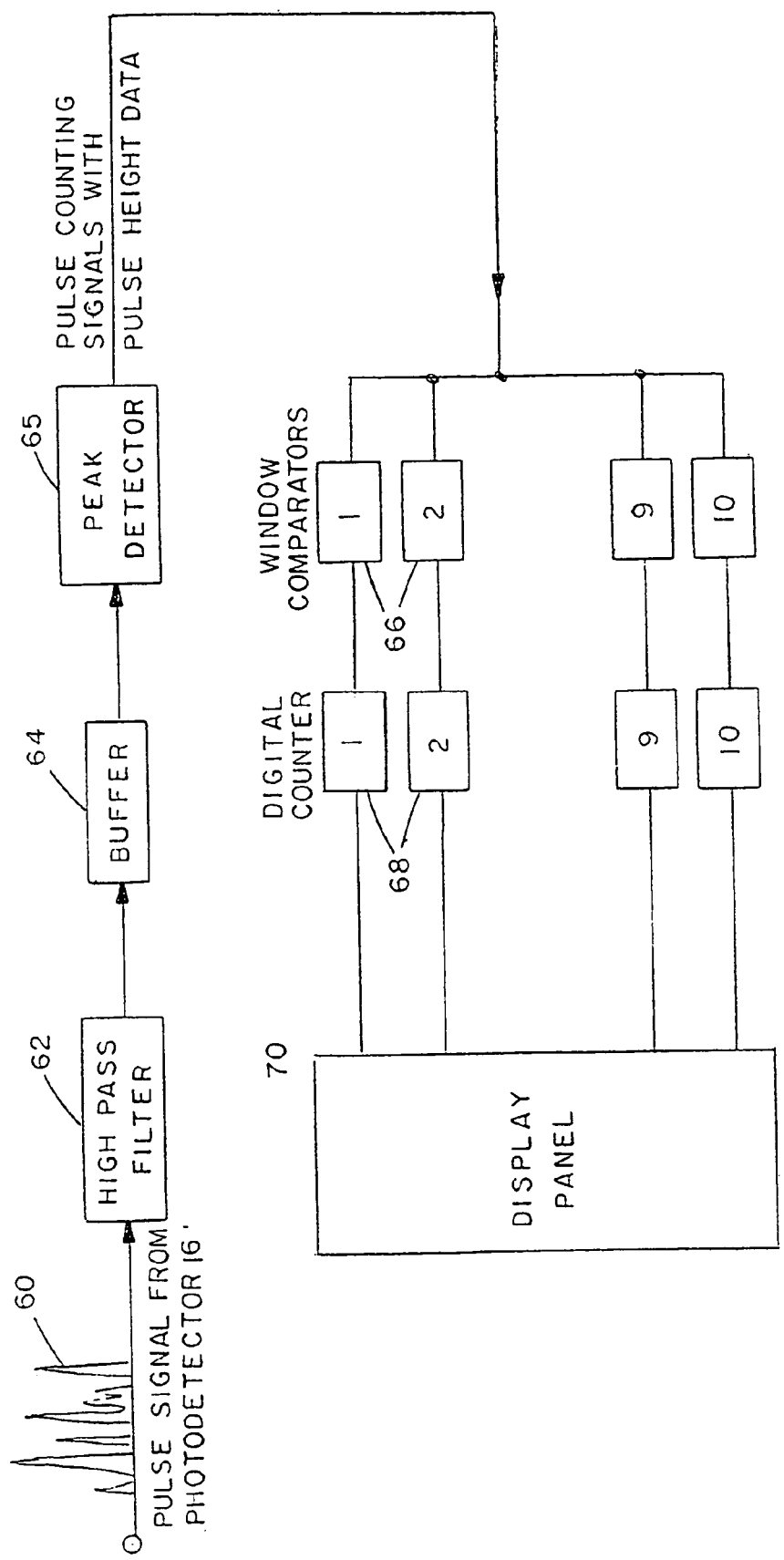
FIG. 4 is a block diagram of a pulse height measurement and display circuit.

The output of detector 14 is connected to one input of differential amplifier 18, as indicated in FIG. 3, while the output of detector 16 (which corresponds to the laser diode output) is connected to the other input of the amplifier 18 and the ratio of these signals is output from the amplifier 18. FIG. 4 is a block diagram of the pulse height measurement circuit, making up the converter unit 22, the window comparator unit 24, and the display 25 in an exemplary embodiment of the invention, while FIG. 5 is a schematic illustrating the digital converter unit in more detail. The output of the photodetector will be a pulse signal, for example a signal 60 as illustrated in FIG. 4, of a series of analog pulses, with each pulse representing light scattered by a particle in the air sample, and the height of the pulse being proportional to the particle size. Each incoming pulse from the photodetector passes a high pass filter 62 in order to eliminate the DC background, and then goes through a buffer 64 to a peak detector 65 which will measure the height of the incoming pulse. The output of peak detector 65 will be a series of constant voltage level pulses carrying the pulse height information. One example of a suitable analog to digital converter and peak detector circuit is illustrated in more detail in FIG. 5, with FIG. 5A illustrating pulse outputs at various points in the circuit. The output signal "PEAK OUT" in FIG. 5A is sent to the window comparator unit for classification. The other pulses illustrated in FIG. 5A are timing and enabling signals to tell the window comparator to take and store the count.

The window comparator unit has a series of window comparators 66 (labeled 1–10 in FIG. 4 by way of example) each designed to detect pulses in a predetermined voltage range (window voltage). Each window comparator 66 will send a signal to its associated digital counter 68 only if the incoming pulse height is within its window voltage (e.g. 5 mV to 7.5 mV for comparator #5). The outputs of the counters 68 are connected to a display panel 70 which will display particle numbers in each particle size bin. Thus, the output display unit 25 may comprise a bar graph lit by light emitting diode (LED) arrays, with the LEDs being lit up in sequence for each particle size based on input from the associated counter, to produce a histogram of the particle size distribution. The bar graph may be in different colors for the different particle sizes. The outputs may also, or alternatively, be connected to a computer programmed to display a histogram of the particle size distribution on its display screen.

The window comparator unit 24 has a plurality of comparators 66 and counters or bins 68 for counting pulses corresponding to particle sizes in the range of interest. In FIG. 4, ten such bins are shown. However, fourteen bins may be provided for particle sizes from one to seven microns, at a 0.5 micron spacing. A smaller or greater number of comparators and counters may be provided if a smaller or larger size range is required, for example a more limited pathogen size range of 1 to 5 µm. FIG. 6 illustrates an example of a histogram of particle size distribution. Although this indicates a distribution in the range from 1 to 19 µm, it will be understood that the control unit may be programmed to display a particle size distribution histogram over the smaller range of 1–7 µm as discussed above. The output of control unit 25 may also be connected to a visible and/or audible alarm device 28, such as an alarm light on the front of the housing and a buzzer or the like.

Any suitable software may be used to generate the output display histogram, such as LabView software available from National Instruments Corporation of Austin, Tex. This software may also be used to produce an output to activate an audible alarm 28 if the number of counts in a size range corresponding to a pathogen or bio-agent particle size exceeds a predetermined level above the normal ambient level. This will help to reduce or even eliminate false alarms. The output of the computer may also be used to trigger a more elaborate bio-agent detection device, such as a PCR based anthrax detection apparatus. This combination detection scheme will be cost effective and will further reduce the risk of a false alarm.

In a modified arrangement, the histogram of the airborne particle size distribution may be compared to that of known weaponized bio-agents, since the processing procedure for such agents is known to have a signature size distribution unique to the machinery used in the process. Thus, the detector system of this invention can provide forensic information on the possible origin of the bio-agent manufacturer.

As noted above, the most probable bio-agents for use in a terrorist attack have size ranges from 1 µm to 7 µm. Table 1 below shows the characteristics of Category A bio-terrorist agents, as specified by the Center for Disease Control:

TABLE 1

Category A bio-terrorist agents

| AGENT | SIZE CHARACTERISTICS |
| --- | --- |
| *Bacillus Anthracis* | Rod shape: width 1.0–1.2 µm, length 3.0–5.0 µm (spore 1.0 × 1.5 µm) |
| *Yersinia pestis* (plague) | Oval 1.0–2.0 µm |
| *Clostidium botulinum* | Rod shape: width 0.8–1.3 µm, length 4.4–8.6 µm |
| *Francisella tularensis* | Rod shape: width 0.2 µm, length 0.7 µm. |

There exists in environmental air only a very small and constant concentration of naturally occurring airborne particles in the size range of 1 µm to 7 µm. The particle size ranges of smog incursion in metropolitan areas and sudden growth of local dust source are peaked at 0.3 µm and 5 µm, respectively. Pollens and other allergens can also be present in the air during blooming seasons, and the size range of allergen particulates is from 5 to 50 µm. Thus, none of these naturally occurring airborne particles are in the typical size range of weaponized bio-agents (1 to 7 µm). The detector system of this invention is therefore designed to detect particles in this specific size range and produce an output representing the range of particle sizes detected at 0.5 µm intervals. Any sudden and localized increase in the number of airborne particles within this size range most likely signifies an intentional release of hostile bio-agents or pathogens. The system can be set up to detect and store a natural background level of particles within the size range of interest, and then use this as a comparison level for subsequent output histograms, in order to activate the alarm on detection of a sudden increase. The particle size distribution histogram of FIG. 6 indicates a probable hazardous situation where the number of particles detected in the size range of 1 to 7 μm is way over normal levels.

Although the pathogen detector system of this invention will not identify the particular species of pathogen, it will serve as a sensitive and cost-effective warning of an airborne bio-agent attack because of the relative scarcity of airborne particles in the range of interest in normal meteorological conditions. Any particles within this range can penetrate the human lungs and be potentially harmful or even fatal for those inhaling them. The alarm provides a warning for individuals in the vicinity to evacuate the area immediately, reducing the exposure to such agents.

The same detection system and method can also be used to detect hazardous levels of potentially harmful dusts in manufacturing facilities. Harmful asbestos fibers are in the size range of 5 μm, having a typical length of 5 μm or longer and a diameter of 1–2 μm. Beryllium dusts are also harmful when breathed into the lungs, which will happen if they are in the 1–5 μm range. The detection system of this invention could be provided in buildings containing asbestos, or when workers are working in such buildings, to provide a warning signal when an unusual spike in the 1 to 5 μm range is detected, which may indicate harmful levels of asbestos fibers in the air. Similarly, the detector may be used in the vicinity when workers are machining beryllium parts, in order to give a warning signal if the number of particles in the 1 to 5 μm size range suddenly increases, indicating the possible presence of harmful levels of beryllium dust. Even though the detector cannot differentiate asbestos or beryllium dusts from non-harmful particles in the same size range, any sudden increase in detected particle levels in this size range when working with asbestos or beryllium will provide an indication of a potentially hazardous situation requiring evacuation of the area and further testing.

In the detector system described above, a two stage detection and discrimination process is used, with the optical portion 10 of the system first eliminating light scattered outside a predetermined angular range incorporating the particle size range of interest. Subsequently, detected output pulses are discriminated according to pulse height, the number of pulses of each height are counted and converted to particle size within 0.5 μm, and the results are displayed as a histogram, with a new histogram being generated at suitable time intervals to illustrate changing particle distribution conditions. However, instead of displaying a particle size distribution histogram, the optical portion of the detector apparatus may alternatively be arranged to direct only that part of the scattered light signal corresponding to a particle size range of 1 to 7 μm to the detector 14, and the remainder of the system is then arranged to emit an alarm signal if the output of the detector exceeds a predetermined threshold level. This will provide a less accurate output, and does not provide any discrimination of particle sizes within the detected size range, but can still give a relatively accurate warning of the presence of an unusually large number of particles within a size range corresponding to known airborne pathogens. The optical assembly 10 of FIG. 1 would only have to be modified to provide a larger central blocking area to block light scattered by particles having a size greater than 7 μm, and the output circuitry would be modified to provide a threshold level discriminator at the output of the detector, and to provide an output signal from the discriminator to activate an alarm if the detected signal is above the selected threshold.

The pathogen detector of this invention can be used in various applications. It may be implemented as a portable, hand-held detector for field personnel. In this case, an outer housing will hold the optical unit as well as the electrical circuitry to count particles in the range of airborne pathogens, and will have an LED display of the current particle counts for each particle size. It will also incorporate an audible alarm and a warning light for laser low power condition. In this case, the detector will be battery powered. A stand-alone, desk top version may also be provided for use in office buildings or the like. This will be similar to the field version, but will be powered from a standard electrical wall socket via an AC/DC converter. In the latter case, the detector will be intended to provide protection from bio-agent contaminated letters or packages in office desk top settings.

The detector may be part of a multiplexed system for building security, comprising a number of detectors in different rooms linked to a central monitoring computer or control station. The control station can be programmed to monitor the particle counts from each room, and to analyze the origin of any unusual increase in pathogen-size particles, and to predict the potential spread pattern within the building. Larger grid systems may be used in large building complexes, such as military bases or city blocks. The detectors may have radio transmitters for transmitting data to a central control station which again can analyze the origin of any detected increase in potential bio-agent particles, and the potentially spread of any bio-agent plume.

The pathogen detector system and method of this invention is compact, inexpensive, and can be provided in a rugged, hand-held unit for early warning of the presence of potentially harmful pathogens such as airborne biological warfare agents or harmful dusts such as asbestos fibers or beryllium dust. Although the system does not necessarily indicate the exact pathogen, it does provide an immediate indication of potentially harmful pathogens and a warning to evacuate and sterilize the area. Also, as noted above, the histogram of particle size distribution may be sufficient to indicate the type of bio-hazard and even its potential source.

Although an exemplary embodiment of the invention has been described above by way of example only, it will be understood by those skilled in the field that modifications may be made to the disclosed embodiment without departing from the scope of the invention, which is defined by the appended claims.

We claim:

1. A pathogen detector system, comprising:
an outer housing having a sample area for containing environmental air;
a light source on one side of the sample area for directing a focused beam of light through the sample air, whereby portions of the beam of light are scattered at various angles by particles of various sizes present in the sample area, and an unscattered portion of the beam of light remains unscattered;
a beam blocking device on the opposite side of the sample area for blocking at least the unscattered portion of the beam of light and directing at least part of the scattered light along a light path;
a first photodetector positioned in the light path after the beam blocking device for detecting light directed by the beam blocking device onto the detector, and producing an output spectrum representing scattering intensity in which the size of each peak is proportional to particle size;

a reflector positioned in front of the beam blocking device in the path of the unscattered portion of the light beam for reflecting at least part of the unscattered portion in a second light paths and a second photodetector positioned to detect light reflected from the reflector;

a differential element responsive to said first and second photodetectors to provide a pulse signal having a scattering peak intensity;

a pulse height discriminator using the scattering peak intensity to characterize particle size, such that the size distribution of airborne particles detected in the air sample at a given time is obtained; and an alarm unit connected to the pulse height discriminator for providing a warning signal if the number of particles within a predetermined pathogen size range of approximately 1 to 7 µm exceeds a predetermined normal level.

2. The system as claimed in claim 1, including a processing unit connected to the output of the pulse height discriminator for processing the particle size distribution at a given time, based on the height of each pulse, producing a histogram of the airborne particle size distribution, and displaying the histogram on an output device.

3. The system as claimed in claim 1, including a power monitor connected to the output of the second photodetector for detecting decrease in light source output power, and an alarm device connected to the power monitor for producing an alarm signal if the light source power falls below a predetermined level.

4. The system as claimed in claim 1, wherein said differential element comprises a differential amplifier connected to the outputs of the two photodetectors for dividing the output of the first photodetector by the output of the second photodetector, the differential amplifier having an output connected to the pulse height discriminator.

5. The system as claimed in claim 1, including a transparent partition slide positioned between the sample area and the beam blocking device.

6. The system as claimed in claim 5, wherein the partition slide is removably mounted in the housing.

7. A detector apparatus for detecting pathogen particles in a size range of approximately 1 to 7 µm in environmental air, comprising:

a light source for directing a focused beam of light through a sample of environmental air, whereby a first portion of said light beam remains unscattered and a second portion of said light beam is scattered at various angles by particles of various sizes present in the air sample, the scattering angle and scattering cross-section being dependent on the particle size;

a beam separating device for separating a predetermined part of the light beam corresponding to light scattered by particles within a predetermined size range from the remainder of the light beam and directing the separated part of the light beam along a light path;

a first phototdetector positioned in the light path for detecting said separated part of the light beam and producing a corresponding output signal of electrical pulses representing scattering intensity in which the size of each pulse is proportional to particle size;

a reflector positioned in front of the beam separating device in the path of the unscattered portion of the light beam for reflecting at least part of the unscattered portion in a second light path, and a second photodetector positioned to detect light reflected from the reflector;

a differential element responsive to said first and second photodetectors to provide a pulse signal having a scattering peak intensity;

a pulse height discriminator for using the peak intensity to characterize particle size; and a control unit connected to the discriminator output for generating an alarm signal if the detected number of particles within a range of approximately 1 to 7 µm in size exceeds a predetermined value.

8. The apparatus as claimed in claim 7, including a processing unit connected to the output of the pulse height discriminator for processing the particle size distribution at a given time, based on the height of each pulse, and producing an output comprising a histogram of the airborne particle size distribution, and a display device connected to the output of the processing unit for displaying the particle size distribution histogram.

9. The apparatus as claimed in claim 7, including a power monitor connected to the output of the second photodetector for detecting decrease in light source output power, and an alarm device connected to the power monitor for producing an alarm signal if the light source power falls below a predetermined level.

10. The apparatus as claimed in claim 7, wherein said differential element comprises a differential amplifier connected to the outputs of the two photodetectors for dividing the output of the first photodetector by the output of the second photodetector, the output of the differential amplifier having an output connected to the pulse height discriminator.

11. The apparatus as claimed in claim 7, including a transparent partition slide positioned between the sample area and the beam separating device.

12. A method of detecting airborne pathogens, comprising the steps of:

directing a light beam from a light source through a sample of environmental air such that a first portion of the light beam is scattered by particles present in the sample and a second portion remains unscattered;

receiving both portions of the light beam which have passed through the air sample and directing the light beam portions onto a beam blocking device;

blocking at least the second portion of the light beam at the beam blocking device and directing at least part of the first portion of the light beam onto a first detector;

measuring the pulse height of electrical pulses output from the first detector;

reflecting at least part of the second portion of the light beam onto a second detector, connecting the output of the second detector to a power monitor for detecting decrease in light source output power;

counting the number of pulses of each pulse height in a predetermined time interval;

converting the pulse heights to particle sizes; and producing an alarm signal if the number of pulses detected within a predetermined size range corresponding to pathogen-size particles is exceeded; or if the light source power falls below a predetermined level.

13. The method as claimed in claim 12, wherein the predetermined size range is approximately 1 to 5 µm.

14. The method as claimed in claim 12, wherein the predetermined size range is from approximately 1 μm to 7 μm.

15. The method as claimed in claim 12, further comprising the steps of converting the data of number of pulses for each particle size into a histogram of the detected particle size distribution, displaying the histogram on an output display device, and repeating the conversion and displaying steps at predetermined intervals for new air samples.

16. The method as claimed in claim 15, further comprising the step of comparing the histogram to known bio-agent particle size distributions, and activating an alarm if the detected distribution matches any known bio-agent particle size distribution.

17. The method as claimed in claim 12, further comprising the step of blowing air through the sample area continuously to monitor changing conditions in a surrounding area.

18. The method as claimed in claim 12, further comprising the step of placing a transparent partition slide between the sample area and beam blocking device to prevent dust from entering optical components.

* * * * *